United States Patent [19]

Choksi

[11] Patent Number: 4,677,987

[45] Date of Patent: Jul. 7, 1987

[54] GAS SAMPLING APPARATUS FOR CAPNOGRAPHY

[75] Inventor: Pradip V. Choksi, Northridge, Calif.

[73] Assignee: SpaceLabs Inc., Redmond, Wash.

[21] Appl. No.: 852,859

[22] Filed: Apr. 16, 1986

[51] Int. Cl.$^4$ .............................................. A61B 5/08
[52] U.S. Cl. ................................. 128/719; 73/863.58; 73/863.81; 422/84
[58] Field of Search .............. 128/716, 718, 719, 725, 128/730; 422/84; 73/863.58, 863.81, 863.85, 864.73

[56] References Cited

U.S. PATENT DOCUMENTS

| | | | |
|---|---|---|---|
| 3,035,569 | 5/1962 | Dubsky et al. | 128/718 |
| 4,456,014 | 6/1984 | Buck et al. | 128/719 |
| 4,558,709 | 12/1985 | Aida et al. | 128/719 |

Primary Examiner—Lee S. Cohen
Attorney, Agent, or Firm—Lawrence S. Levinson; Robert E. Lee, Jr.

[57] ABSTRACT

A connector and sampling line for obtaining sample gases from a patient's exhaled gas stream present in an air tube coupled to the patient is disclosed. The sampling line comprises a sampling end portion having an open end and at least one hole in a wall of the end portion. A tubular shaped connector through which the gas stream passes along a first path includes a hollow cylinder coupled to the wall of the connector and protruding therefrom. The hollow interior of the connector communicates with ambient atmosphere through a distal open end and to the interior of the tubular portion of the connector through a hole in the connector wall. The sampling line includes a reinforced portion adjacent the sampling end portion for reinforcement. The hollow cylinder has an interior diameter large enough to receive the reinforced portion and substantially larger than the hole in the connector wall which hole is large enough to receive the sampling end portion. The cylinder interior is tapered to receive and frictionally engage the reinforced portion of the sampling tube.

3 Claims, 8 Drawing Figures

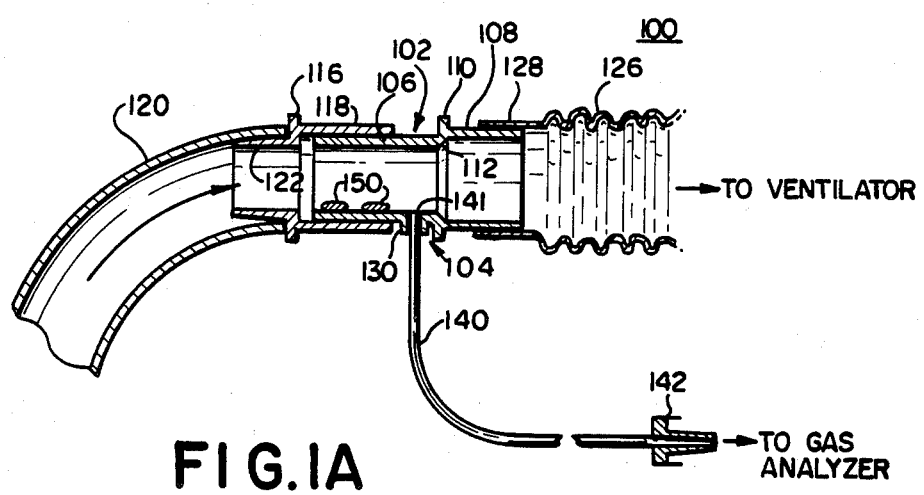
FIG. IA
(Prior Art)
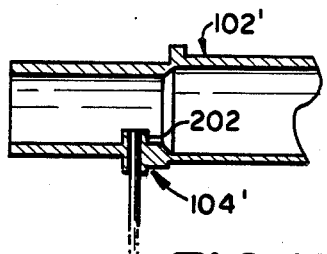
FIG. IB
(Prior Art)
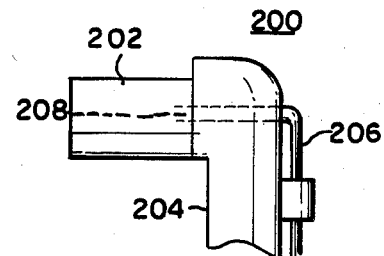
FIG. 2
(Prior Art)
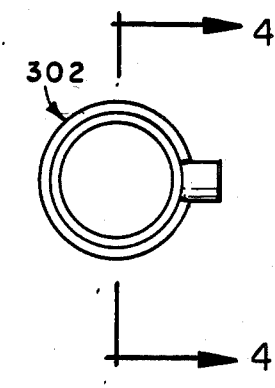
FIG. 3
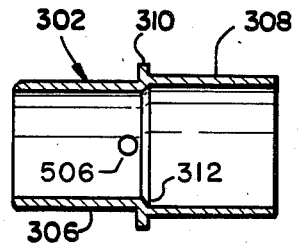
FIG. 4

GAS SAMPLING APPARATUS FOR CAPNOGRAPHY

BACKGROUND OF THE INVENTION

The present invention relates to an apparatus for gas sampling in capnography, more particularly to an airway adapter with a gas sampling line.

Capnography is the measurement of the level of carbon dioxide in the exhaled breath of a patient. This information is important in the diagnosis of a patient's pulmonary function. Usually measurements are continuous and carbon dioxide levels are displayed as a curve on a CRT display.

Capnographic measurements are performed by aspirating a continuous stream of gas from the patient's exhalation line which stream is fed through an aspirating line to an infra red sensor. The flow rate of the sample stream is usually 200 ml/min or less. In order to minimize dampening of the signal, the internal volume of the sampling line is kept as small as possible (about 2 ml.). The inside diameter of the sampling line is often 1 mm (0.040 inches) or smaller. The exhaled gases leave the patient at 99° Fahrenhait and virtually 100 per cent relative humidity. Some condensation occurs in the in-line connector and additionally in the sampling line as the gas continues to cool to room temperature (usually around 70° F.). The small diameter of the sampling line is very susceptible to clogging by mucus expectorated by the patient and the liquid condensate.

There are several prior art combination airway adapter and sampling tube products available in the market place made or sold by companies such as Engstrom, Allegheny, Novametrix, Biochem, Gould, Puritan-Bennett, Carburos-Melabicos, Datex, Godart, Ohmeda, Traverse Medical, Sensormedics and Siemens-Elena. Typically, the product includes an in-line connector, i.e. a connector, usually plastic, which fits within the exhalation tube of the patient, and a sampling tube coupled between the connector and the sensing instrument. The connector is usually of T-configuration or an elbow. The sampling line is usually nylon or Nafion or vinyl and may or may not be equipped with fittings such as luer fittings at one or both ends. Sometimes a filter and/or water trap is provided usually between the sampling line and the instrument. Some systems are equipped with means to reverse the gas flow to clear a clog.

In the Datex made product, sold by Puritan-Bennett and Carburos-Melabicos, the in-line connector is a molded fitting with an integrally bonded tube that extends inside by about a quater inch. The Ohmeda product comprises an in-line connector which is an elbow fitting with a sampling line extending inside for about ⅜ of an inch. The line appears to be pressed into the elbow approximately coaxially aligned with one of the legs of the elbow.

SUMMARY OF THE INVENTION

The present invention relates to an airway adapter for obtaining a sample gas flow from a patient's exhaled gas flow. It includes a hollow sampling line having an open end and at least one hole in the wall thereof spaced apart from the open end. Means are provided for positioning the open end and at least one hole within the gas flow.

In the preferred embodiment, the means comprises a connector having an elongated main tubular portion along which the gas flow moves. The connector further includes a hollow cylinder attached to a wall of the tubular portion and portruding outwardly. The interior of the cylinder communicates with the ambient atmosphere at a distal end thereof and with the interior of the tubular portion through an aperture in the wall of the tubular portion.

The cylinder and aperture are adapted to receive the sampling line whereby the open end of the line and the at least one hole protrude into the interior of the tubular portion. The sampling line comprises a reinforced portion which is spaced apart from the open end and at least one hole. The adapter cylinder's internal diameter is large enough to accept the reinforced portion of the sampling line in frictional engagement therewith while the diameter of the aperture in the wall of the tubular portion is large enough to accept the sampling end of the sampling tube but not the reinforced portion. In the preferred embodiment, the interior of the adapter cylinder is tapered to accept the reinforced portion in frictional engagement.

BRIEF DESCRIPTION OF THE DRAWINGS

FIG. 1A is an example of a first prior art connector and sampling tube combination for use in capnography.

FIG. 1B shows the prior art connector of FIG. 1A slightly altered.

FIG. 2 is an example of a second prior art connector and sampling tube combination for use in capnography.

FIG. 3 is an end view of the preferred embodiment connector of the present invention.

FIG. 4 is an elevational cross sectional view of the connector of FIG. 3 taken along the lines and arrows 4—4 in FIG. 3.

DETAILED DESCRIPTION OF THE DRAWINGS

Figure 5:
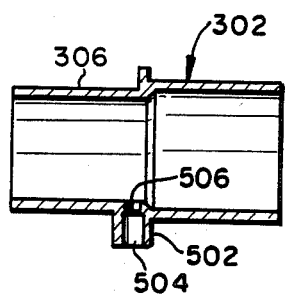
FIG. 5 is an elevational cross sectional view of the connector of FIG. 3 taken along the lines and arrows 5—5 in FIG. 4.

Referring to FIG. 1, a prior art connector and sampling tube combination designated generally 100 is shown comprising an in-line connector 102 with a side port 104. The connector has a first hollow tubular portion 106 coupled to a second hollow tubular portion 108 having a larger internal and external diameter than portion 106. Where the two tubular portions meet, there is formed on outer annular ring 110 of outside diameter which is larger than the outside diameters of the first and second tubular portions. On the inside where the two tubular portions meet, a ledge 112 is formed where the smaller internal diameter of the first tubular portion meets the larger internal diameter of the second tubular portion.

An adapter 116 is shown which fits over the first tubular portion at the end 118 and fits within an airway tube 120 at its other end 122. The air way tube is connected to the patient at its other end. A flexible ribbed ventilator tube 126 has one end 128 fitted over the second tubular portion 108 of the connector 102 and its other end connected to the breathing apparatus (not shown).

The side port 104 comprises a short hollow cylinder 130 formed in the side of the first tubular portion 106 just before the ledge 112 and protruding outwardly therefrom. The hollow interior of the connector is in communication with the ambient atmosphere through the cylinder 130.

The short hollow cylinder 130 is adapted to receive a relatively small diameter sampling tube 140 which is inserted into the short cylinder 130 at one end 141 and which is equipped with a fitting 142 at its opposite end for connection to a gas analyzer (not shown). In the embodiment shown in FIG. 1A the end 141 does not protrude into the interior of the connector. The connector 102 could be equipped with a fitting at port 104 to receive a mating fitting on the end of the tube 140.

FIG. 1A also shows liquid condensate and other material, such as mucus 150 resting on the bottom of the inside wall of tubular portion 106. As gas is aspirated from the air way tube and the interior of the connector 102 through the side port 104, the liquid condensate and mucus can easily enter the sampling line 140 and clog it.

In FIG. 1B, the side port 104' of the connector 102' protrudes into the interior about $\frac{1}{4}''$ at 202. This will aid in preventing clogging but is not completely satisfactory.

In FIG. 2, an elbow shaped connector designated generally 200 found in the prior art comprises a first hollow cylindrical leg 202 coupled to a second hollow cylindrical leg 204 with the axis of the first leg perpendicular to the axis of the second leg. A sampling line 206 with open end 208 is pressed through a hole in the elbow in a direction lying substantially along the axis of the first leg 202 and protruding a distance into the elbow connection.

Referring to FIGS. 3 through 5, FIG. 3 is an end view, viewed from the end with largest diameter, of the in-line connector portion 302 of the present invention. It comprises a first hollow tubular portion 306 coupled to a second hollow tubular portion 308 having a larger internal and external diameter than the first hollow tubular portion. Where the two tubular portions meet, there is formed an outwardly protruding annular ring 310 of outside diameter which is larger than the outside diameters of the first and second portions. On the inside where the two tubular portions meet, a ledge 312 is formed where the smaller internal diameter of the first tubular portion 306 meets the larger internal diameter of the second tubular portion 308. The connector is adapted to fit within an endotracheal tube at one end and within a ventilation tube at the other.

The connector further comprises a side port formed by a short hollow cylinder 502 integrally formed with the wall of the first tubular portion 306 and extending outwardly therefrom. One end 504 of the cylinder opens up to the ambient atmosphere while the other end opens up through an aperture 506 in the tubular wall into the interior of the connector 302. The diameter of the cylinder 502 is larger than the diameter of the aperture 506 through the tubular wall. In the preferred embodiment, the internal diameter of the cylinder 502 is slightly tapered from 0.130±0.002 inches at the open end 504 to a diameter of 0.120±0.002 inches at the junction with the aperture 506 in the tubular wall. The aperture 506 has a diameter of 0.090 inches.

Figure 6:
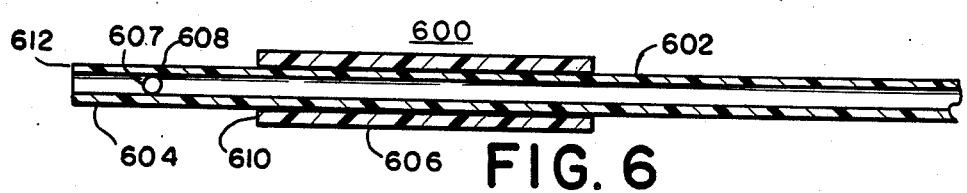
FIG. 6 is a elevational view in partial cross section of the preferred embodiment sampling tube of the present invention.

Referring now to FIG. 6, a preferred embodiment sampling line designated generally 600 for use with the present invention is disclosed. It comprises a length of vinyl tubing 602 having an outer diameter of 0.065±0.001 inches with an internal diameter of 0.040±0.003 inches. Surrounding the tubing 602 for about a length 0.55 inches, starting approximately 0.30 inches from open end 604, is a relatively thick walled reinforcement section of vinyl tubing 606. It is formed over the tubing 602 in such a way that there is no gap at the interface between outer surface of tubing 602 and the inner surface of tubing 606. The outer diameter of tubing 606 is 0.125±0.003.

The sampling tube 602 has a 0.040±0.002 inch hole 607 stamped through the length 608 between the end 610 of reinforcement section 606 and end 604. In the preferred embodiment the hole is positioned 0.13 inches from end 604. While the hole is stamped through both opposite walls of the tubing it need not be. Only one hole could be made, or two holes across from one another or more than two holes could be placed in section 608.

The air sampling tube 600 is inserted into the cylinder of the connector until the reinforcement tubing is compressed by the narrowing interior walls of the cylinder 502. Note that the cylinder walls taper from 0.130 to 0.120 while the reinforcement tubing section 606 is 0.125 inches in diameter. The reinforcement tubing is flexible and as it is pressed into the cylinder 502 it engages the sloping interior walls and becomes frictionally engaged therein. In the preferred embodiment the reinforced tubing portion 606 is glued in place within the cylinder 502.

Figure 7:
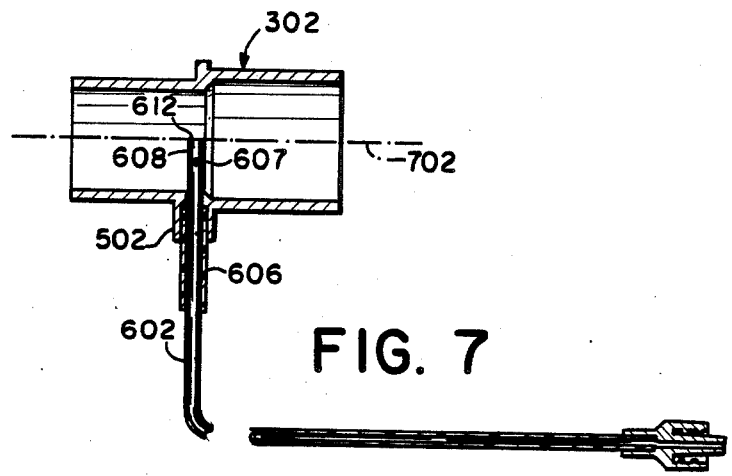
FIG. 7 is a cross sectional view of the preferred embodiment connector and sampling tube of the present invention shown coupled together.

The length 608 of the inner tubing passes through the hole 607 in the wall of the connector and protrudes into the interior of the connector where the tip 612 is roughly located at the center line 702 of the connector. See FIG. 7.

The interior of the connector is in communication with the interior of the inner tubing 602 through the open end 604 of the tubing and the holes 607 in the length 608. As long as at least one hole is open, the gas will take the path of least resistance and enter the tubing through the open hole and liquid will not be aspirated.

The reinforced double tubing 606 at the sampling line to in-line connector joint avoids kinking and tearing. Also, the tapered interior cylinder 502 adapted to receive the reinforced section 606 of the sampling line 602 provides a quick release positive engagement without the need for fixtures or connectors on the in-line connector and the end of the sampling tube.

It should be pointed out that catheters exist, particularly for use in peritoneal dialysis, which are multi-lumen catheters with a plurality of openings in the side walls for introducing liquid and then removing liquid from the stomach of a patient. But no such multi lumen or multi-opening approach has been used in air way sampling as a device for separating gas from liquid so as to avoid aspirating liquid.

What is claimed is:

1. An apparatus for obtaining a sample gas flow from a patient's exhaled gas stream present in an air tube coupled to said patient comprising:
    a connector adapted for insertion in said air tube, said connector providing a pathway for said gas flow, said connector including:
    an elongated main tubular portion along whose axis said gas flow pathway is generally parallel; and
    a hollow cylinder coupled to a side wall of said main tubular portion and protruding outwardly therefrom, the interior of said cylinder communicating with the ambient atmosphere through a distal open end and with the interior of said main tubular portion through an aperture in the wall of said main tubular portion, said hollow cylinder having an internal diameter substantially larger than the diameter of the aperture in said tubular portion wall;

a hollow sampling line detachably coupled to said connector comprising:

a sampling end portion with a first open end and at least one hole spaced apart from said open end through the wall of said sampling end portion; and a reinforced portion for reinforcing said sampling line, said reinforced portion spaced apart from said sampling line open end and said at least one hole, said reinforced portion having an outer diameter substantially larger than the diameter of said sampling end portion, said sampling end portion comprising the length of said sampling line from the first open end to the start of said reinforced portion, said reinforced portion adapted to frictionally engage the interior of said hollow cylinder when said sampling line is coupled to said connector, the length of said sampling end portion being long enough such that said first open end and said at least one hole extend through said aperture in the wall of said main tubular portion into the patient's exhaled gas stream.

2. The apparatus of claim 1 wherein said internal diameter of said cylinder is tapered from a diameter slightly larger than said reinforced portion diameter at said distal end and slightly smaller than said reinforced portion diameter where the cylinder meets the wall of the tubular portion.

3. The apparatus of claim 1 wherein the length of said sampling end portion is such that said open end is positioned substantially at the center of said gas flow pathway when said sampling line is coupled to said connector.

* * * * *